April 28, 1964 E. S. BOERNER Plant Pat. 2,396
CHRYSANTHEMUM PLANT
Filed May 13, 1963
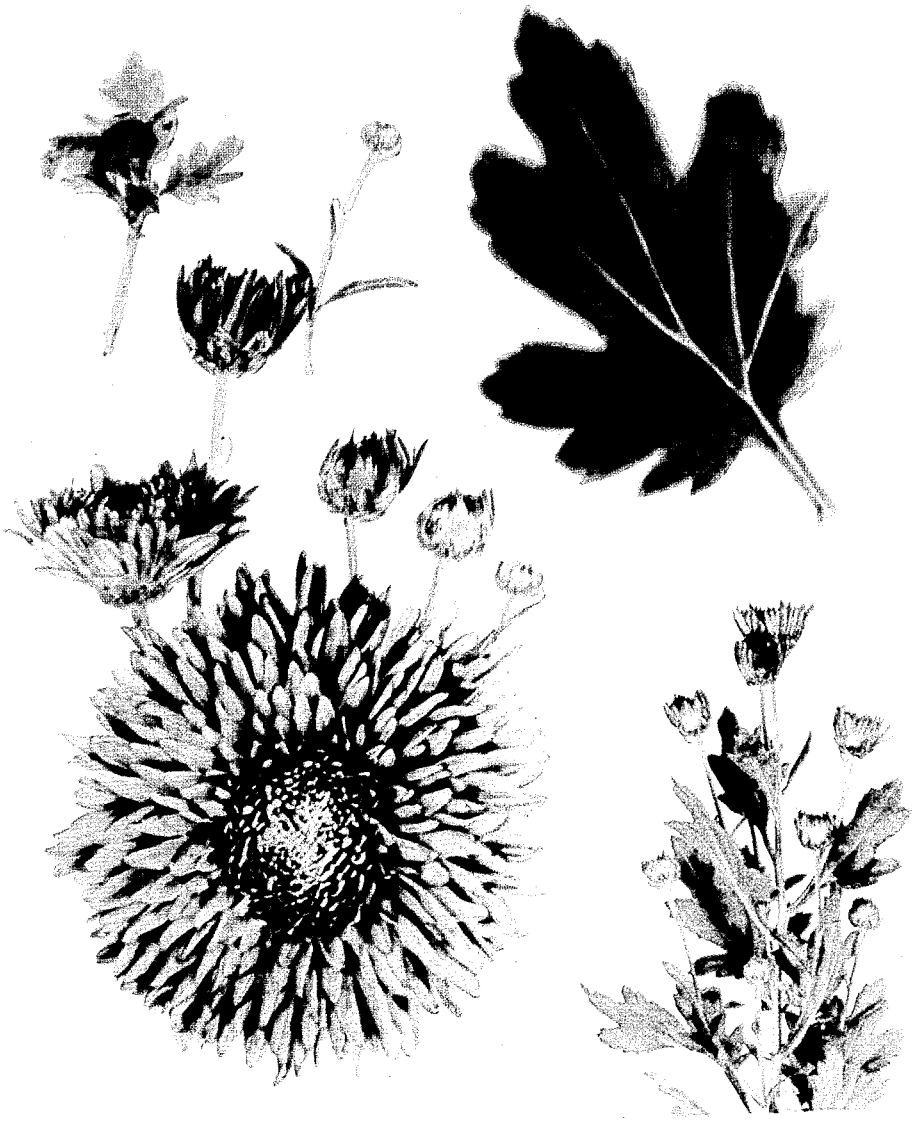
Inventor.
E. S. Boerner
By: Robb & Robb
Attorneys.

United States Patent Office

Plant Pat. 2,396
Patented Apr. 28, 1964

2,396
CHRYSANTHEMUM PLANT

Eugene S. Boerner, Newark, N.Y., assignor to Jackson & Perkins Company, Newark, N.Y., a corporation of New York Filed May 13, 1963, Ser. No. 280,172
1 Claim. (Cl. Plt.—82)

The present invention relates to a new and distinct variety of chrysanthemum plant of the decorative class, which was originated by me by crossing the variety known as "Robin" (Plant Patent No. 1,307) with the variety known as "Macaw" (Plant Patent No. 1,609).

The primary objective of this breeding was to produce a new chrysanthemum variety in which there is combined the excellent plant type of the parent variety "Macaw" with the flower color and size of that which is characteristic of the parent variety "Robin." This objective was fully achieved along with other desirable improvements, as evidenced by the following unique combinations of characteristics which are outstanding in the new variety and which distinguish it from its parents, as well as from all other varieties of which I am aware:

(1) A strong, upright and winter hardy plant habit;
(2) Large flower size;
(3) A double and thick flower form; and
(4) A distinctive and attractive general color tonality of the flowers corresponding to Nopal Red, very lightly overcast with Carmine.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black and white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, during the latter part of the month of October:

Parentage: Seedling.
*Seed parent.*—"Robin."
*Pollen parent.*—"Macaw."
Classification: Decorative.
Growth: Strong; upright.
Cold resistance: Winter hardy and frost resistant in northern New York State.

Blooming period: From early October until freezing weather.

*Flower*

Bud:
*Color.*—When petals first divide—Pomegranate Purple, Plate 12, very lightly overcast with Tyrian Rose, Plate 12. When petals begin to unfurl—Van Dyke Red, Plate 13, very lightly overcast with Bordeaux, Plate 12. When half-blown: inside—Carmine, Plate 1, very lightly overcast with Oxblood Red, Plate 1; outside—Nopal Red, Plate 1, very lightly overcast with Scarlet Red, Plate 1.
*Peduncle.*—Color—Light Cress Green, Plate 31. Strength—strong.

Bloom:
*Size.*—5½ inches.
*Stem.*—Strong.
*Form.*—Decorative; thick (from 2½ inches to 3 inches thick).
*Petalage.*—Very double.
*Color.*—Center of flower—Carmine, Plate 1, lightly overcast with Nopal Red, Plate 1. Outer petals—Nopal Red, Plate 1, very lightly overcast with Scarlet-Red, Plate 1. Base of petals—Strontian Yellow, Plate 16. Inside of petals—Nopal Red, Plate 1, very lightly overcast with Carmine, Plate 1. Reverse of petals—Light Ochraceous-Salmon, Plate 15, very lightly overcast with Nopal Red, Plate 1.
*Petals.*—Texture—medium. Form—ovoid.
*Fragrance.*—Characteristic chrysanthemum.

*Plant*

Form: Upright.
Growth: Strong; erect.
Foliage:
*Size.*—From medium to large.
*Quantity.*—Normal.
*Color.*—Upper side—Varley's Green, Plate 18. Reverse side—Light Bice Green, Plate 17.
*Texture.*—Thick; leathery.

I claim:

A new and distinct variety of chrysanthemum plant of the decorative class, substantially as herein shown and described, characterized particularly as to novelty by the unique combination of a strong, upright and winter hardy plant habit, large flower size, a double and thick flower form, and a distinctive and attractive general color tonality of the flowers corresponding to Nopal Red, very lightly overcast with Carmine.

No references cited.